United States Patent
Mühlbauer et al.

(10) Patent No.: US 6,540,395 B2
(45) Date of Patent: Apr. 1, 2003

(54) DYNAMIC MIXER FOR DENTAL IMPRESSION COMPOUNDS

(75) Inventors: Wolfgang Mühlbauer; Hans Hörth; Bernd Detje, all of Hamburg; Guido Meyer, Elmshorn; Sven Meyer, Apensen, all of (DE)

(73) Assignee: Ernst Mühlbauer KG, Hamburg (DE)

( * ) Notice: Subject to any disclaimer, the term of this patent is extended or adjusted under 35 U.S.C. 154(b) by 184 days.

(21) Appl. No.: 09/747,147

(22) Filed: Dec. 22, 2000

(65) Prior Publication Data

US 2001/0005338 A1 Jun. 28, 2001

(30) Foreign Application Priority Data

Dec. 23, 1999 (EP) .............................. 99125804

(51) Int. Cl.$^7$ ................................. B01F 7/00
(52) U.S. Cl. ..................... 366/307; 366/329.1
(58) Field of Search ............... 366/172.1, 172.2, 366/176.1, 181.5, 328.2, 328.3, 329.2, 338, 339, 316, 307, 329.1; 222/145.5, 145.6

(56) References Cited

U.S. PATENT DOCUMENTS

| | | | |
|---|---|---|---|
| 3,051,455 A | * | 8/1962 | Magester |
| 3,226,093 A | * | 12/1965 | Gugel et al. |
| 3,302,832 A | | 2/1967 | Hardman et al. |
| 3,390,814 A | * | 7/1968 | Creighton, Jr. et al. |
| 3,570,719 A | * | 3/1971 | Schiff |
| 3,587,982 A | * | 6/1971 | Campbell |
| 3,767,085 A | * | 10/1973 | Cannon et al. |
| 4,107,793 A | * | 8/1978 | Wallace |
| 4,432,469 A | * | 2/1984 | Eble et al. |
| 4,471,888 A | * | 9/1984 | Herb et al. |
| 4,767,025 A | * | 8/1988 | Gebauer et al. |
| 4,934,827 A | * | 6/1990 | Taschke et al. |
| 4,951,843 A | * | 8/1990 | Paetow |
| 5,249,862 A | * | 10/1993 | Herold et al. |
| 6,244,740 B1 | * | 6/2001 | Wagner et al. |
| 6,311,871 B1 | * | 11/2001 | Binder |

FOREIGN PATENT DOCUMENTS

| | | | |
|---|---|---|---|
| DE | 29 49 369 A | | 6/1981 |
| DE | 42 35 736 C | | 3/1994 |
| DE | 297 05 741 U | | 8/1998 |
| DE | 10015133 | * | 8/2001 |
| EP | 87029 | * | 8/1983 |
| EP | 0 492 412 A | | 7/1992 |
| EP | 603492 | * | 6/1994 |
| EP | 1072323 | * | 1/2001 |
| EP | 1149627 | * | 10/2001 |
| JP | 6-226178 | * | 8/1994 |
| JP | 8-187727 | * | 7/1996 |
| JP | 2001-207996 | * | 8/2001 |
| WO | 00/21652 | * | 4/2000 |
| WO | 01/24919 | * | 4/2001 |

* cited by examiner

Primary Examiner—Charles E. Cooley
(74) Attorney, Agent, or Firm—Alix, Yale & Ristas, LLP

(57) ABSTRACT

The subject of the invention is a dynamic mixer for viscous compositions, in particular for components for dental impression compounds. The mixer consists of a mixer tube, a rotor located in the latter, and an end wall with inlet openings through which the components to be mixed pass into the mixer. In doing so, they first alternately fill chambers arranged on the rotor. The composition then flows out of the chambers through admission openings into the mixing channel, where it can be stirred by mixer blades.

25 Claims, 2 Drawing Sheets

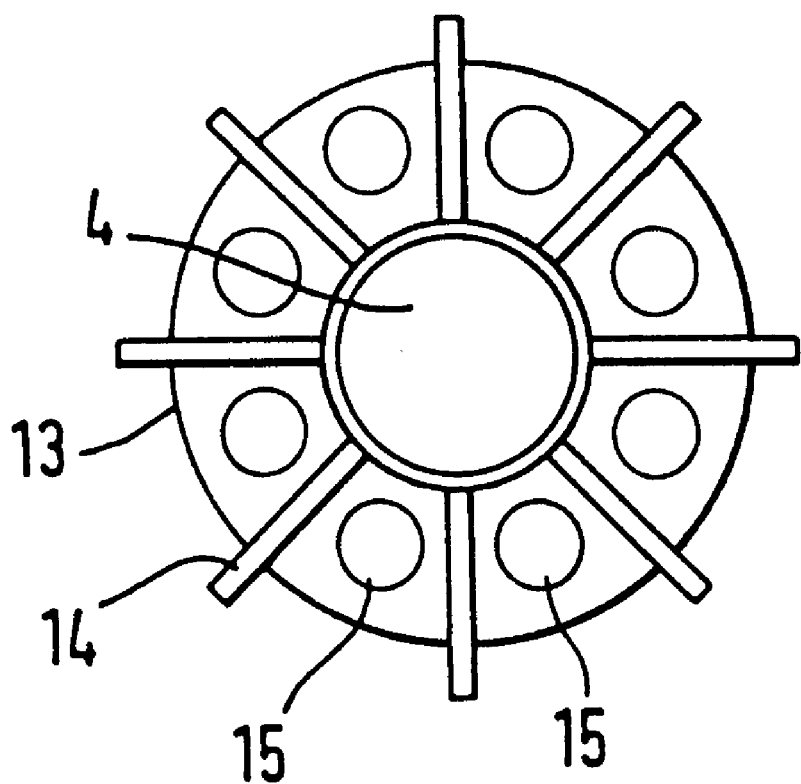

DYNAMIC MIXER FOR DENTAL IMPRESSION COMPOUNDS

BACKGROUND OF THE INVENTION

The invention relates to a dynamic mixer for viscous compositions, in particular for components of dental impression compounds.

It is known (EP-B-492412) to attach a dynamic mixer to a device for dispensing the components which are to be mixed, said dynamic mixer having at the other end an outlet opening for the mixture. It comprises a mixer tube, a rotor which is mounted and can be driven rotatably therein and which, with the mixer tube, delimits a mixing channel of annular cross section, and an end wall with inlet openings through which the components to be mixed pass into the mixing channel. The rotor has mixer blades which are intended to mix together the components flowing through the mixing channel.

SUMMARY OF THE INVENTION

The object of the invention is to improve the mixing effect. Accordingly, the rotor has one or more chambers which are completely or at any rate for the most part open towards one side. These open sides are directed towards the inlet openings in the end wall, so that the components passing through these openings into the mixer are initially received by the chambers. This can involve a single chamber arranged round the entire circumference of the rotor, or a plurality of chambers. Where one chamber is referred to in the text below, this reference will also always cover embodiments having a plurality of chambers, and vice versa.

As they move past the inlet openings, the chambers alternately receive partial quantities of the components, which stack up on each other or accumulate in the chambers. They pass, pre-mixed and/or in rapid alternation, into the mixing channel through outflow opening(s).

The underside of the chamber is advantageously designed as a plate forming the outflow opening or outflow openings. The plate forms the outflow opening(s) advantageously by way of cutouts through which the components are pressed. These cutouts can be of circular shape, for example, or in the form of incisions designed preferably as radially oriented slots. They are expediently distributed uniformly over the underside of the chamber so that deposits not participating in the flow process are minimized.

However, the plate can also form an outflow opening by means of the outer radius of the plate being slightly smaller than the inner radius of the mixer tube. The outflow opening is in this case formed by a gap between the plate edge and the inner surface of the mixer tube. Between the moving outside of the plate and the stationary mixer tube, the composition pressed through this gap is subjected to a shearing stress which promotes mixing.

A plurality of chambers distributed about the circumference are advantageously separated by walls. Distributing the chambers about the whole circumference has the effect that all of the components undergo the stacking process. The walls in the first place ensure more uniform mixing and in the second place ensure that the components emerging from the inlet openings are entrained in small portions.

The total surface area of the outflow opening(s) in relation to the cross-sectional area of the mixing channel is preferably 10 to 50%. Insofar as the cross-sectional area of the mixing channel varies along the mixer tube, this means the cross-sectional area of the mixing channel at the level of the outflow opening(s). With these size ratios, it has been found that, when the components are pressed out through the outflow opening, very good mixing occurs. The mixing is particularly good in the case of a ratio of 25%.

Mixer blades which further improve the mixing are advantageously arranged on the rotor. The mixer blades can be arranged in groups, in which case the mixer blades of one group are each located at the same height of the axis of rotation of the rotor. As regards the mixing result, it is particularly advantageous if the distances between the groups vary along the axis of rotation of the rotor.

Of the area of the rotor under the chamber(s), a length section of at least 10% and expediently not more than 40%, preferably between 15% and 25%, is advantageously free of mixer blades. It has been found that in this area there is substantial interplay between the composition and the inner wall of the mixer tube. This improves the mixing result compared with a continuous arrangement of mixer blades.

Stationary blades are advantageously arranged on the wall of the mixing channel, at the level of the rotor area which is free of mixer blades. This further enhances the interplay between the inner wall of the mixer tube and the composition.

So-called baffles are advantageously arranged on that side of the end wall directed towards the mixing channel, through the inlet openings of which the components pass into the mixing channel. In this way, the free flow of the components in the area between the end wall and the edges of the walls separating the chambers is impeded, thus preventing the components from hardening already in the area of the inlet openings. The mixing is additionally improved because the baffles modify the flow paths and thus effect different flow rates. Where such baffles are present, the walls of the chambers do not strip the components from the walls of the inlet openings but from the baffles.

BRIEF DESCRIPTION OF THE DRAWINGS

The invention is explained in greater detail below with reference to the drawing which depicts an advantageous illustrative embodiment, and in which:

FIG. 6 shows a plan view of an alternative embodiment of the rotor with a plurality of chambers with outflow openings configured as circular cutouts.

DETAILED DESCRIPTION OF THE PREFERRED EMBODIMENTS

Figure 1:
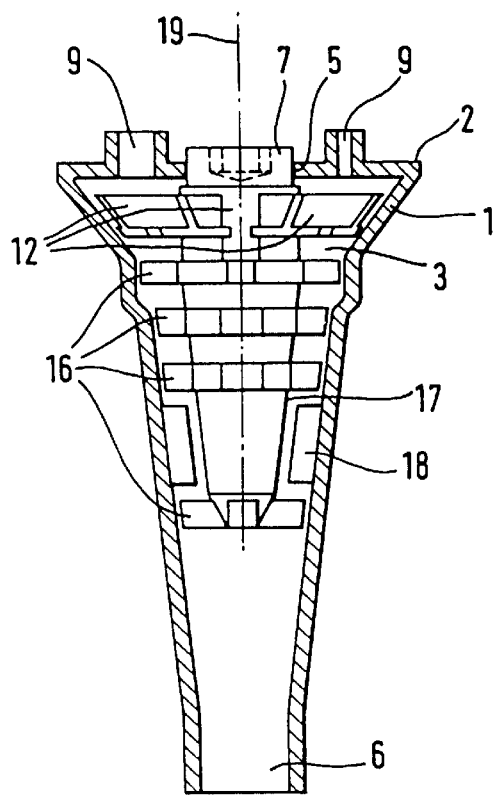
FIG. 1 shows a longitudinal section through a mixer, on an enlarged scale.
Figure 2:
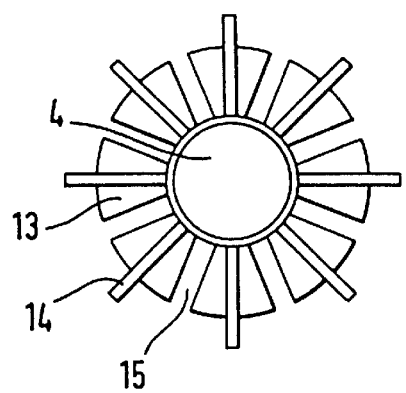
FIG. 2 shows a plan view of the rotor with a plurality of chambers.
Figure 3:
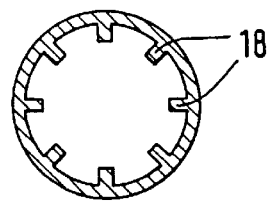
FIG. 3 shows a section through the mixer tube at the level of the area which is free of mixer blades.
Figure 4:
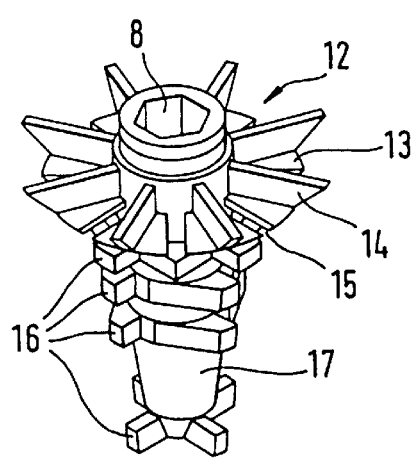
FIG. 4 shows an isometric view of the rotor.
Figure 5:
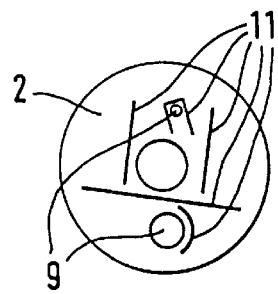
FIG. 5 shows a plan view of the end wall from the direction of the outlet opening.

The mixer comprises a mixer tube 1 which at one end abuts against an end wall 2 and at its other end has an outlet opening 6. The mixer further comprises a rotor 4 whose axis of rotation 19 coincides with the longitudinal axis of the mixer tube 1. The space between the rotor 4 and the mixer tube 1 forms a mixing channel 3 of annular cross section. The end wall 2 has a bearing bush 5 for a rotor plug 7 which protrudes with a coupling attachment designed for example as a hexagon socket.

Arranged on the end wall 2 there are two inlet attachments which can be connected tightly to outlet attachments (not shown) on the dispenser device. On the inner side of the end wall 2 directed towards the rotor 4, they form two inlet openings 9 through which the components to be mixed pass into the mixer. Arranged on the inner side of the end wall 2 there are so-called baffles 11 (not shown in FIG. 1) constituting elongate projections which are in part straight and in part curved. They are arranged in such a way that they screen off the inlet openings 9 from each other. This is intended to ensure that the components cannot already come together and harden in the vicinity of the inlet openings 9. On one of the inlet openings 9 which is designed smaller than the other, the baffles are arranged such that they extend around these openings completely or partially, for example in a U-shape. In this way, the string of component passing through this inlet opening 9 is widened.

The rotor 4 bears chambers 12 adjoining the end wall 2 or the baffles 11. These chambers 12 are delimited by a plate 13 on their side directed away from the end wall 2. On the side of the plate 13 directed towards the end wall 2 there are eight walls 14 which are distributed uniformly about the circumference and each extend from the surface of the rotor shaft 7 as far as the inner surface of the mixer tube 1 and thus separate the chambers from each other.

The rotary movement of the rotor 4, in conjunction with the end wall 2 and the baffles 11, causes the components to come together over a wide surface area. In this way, the chambers 12 are alternately filled with the components. Uniform distribution of the components in the chambers can in this case be promoted by widening of the thinner string at the smaller inlet opening 9. The content of the chambers is then pressed into the mixing channel 3 through eight cutouts 15 which form outflow openings.

The cutouts 15 are designed as radially oriented, elongate slots which each extend from the surface of the rotor shaft 7 as far as the outer edge of the plate 13. There is one cutout 15 in each case between two walls 14. The cutouts 15 can alternatively be configured as circular openings, as illustrated in FIG. 6.

In the mixing channel 3, the composition is mixed together by mixer blades 16 arranged in four groups on the rotor 4. Between the third and fourth groups of mixer blades 16 there is an area 17 in which the rotor 4 is free of mixer blades. In this area, mixing is provided for by stationary mixer blades 18 arranged on the inner surface of the mixer tube 1. After the mixture has passed the last group of mixer blades 16, it leaves the mixing channel 3 by way of the outlet opening 6. The rotor can be designed in a two-jaw configuration with injector plate, the jaws forming the mixer blades and the underside of the plate, while the chambers are formed by the injector plate.

What is claimed is:

1. A dynamic mixer for the components of dental impression compounds, whose one end can be connected to a device for dispensing the components and whose other end has an outlet opening for the mixture, and which comprises a mixer tube, a rotor arranged for rotation within said mixer tube about an axis of rotation, a mixing channel outwardly defined by said mixing tube and inwardly defined by said rotor and of annular cross section, and an end wall with inlet openings for the components, characterized in that the rotor directs the open side of at least one chamber towards the end wall, which at least one chamber in each case has at least one outflow opening, said at least one outflow opening defined by a cutout in a plate projecting radially from said rotor and axially spaced from said end wall such that an axial movement of said components is constricted as said components pass through said at least one outflow opening.

2. Dynamic mixer according to claim 1, characterized in that said cutout is configured as a radially oriented slot.

3. Dynamic mixer according to claim 1, characterized in that said cutout is configured as a circular opening.

4. Dynamic mixer according to claim 1, wherein said dynamic mixer comprises radially projecting groups of mixer blades axially spaced from each other on said rotor and characterized in that the axial spacing between said groups of mixer blades vary along the axis of rotation.

5. Dynamic mixer according to claim 4, characterized in that, a section of said rotor separated from said at least one chamber by said plate is free of mixer blades for an axial distance equivalent to at least 10% of an axial length of said rotor.

6. Dynamic mixer according to claim 5, characterized in that vertical mixer vanes are arranged to project inwardly from an inner surface of the mixer tube in an axial location corresponding to said section of the rotor free of mixer blades.

7. Dynamic mixer according to claim 1, wherein said at least one chamber comprises a plurality of chambers arranged around said axis of rotation and said plurality of chambers are separated from each other by radially projecting walls extending axially from adjacent said end wall to said plate.

8. Dynamic mixer according to claim 7, wherein said mixer comprises baffles projecting from said end wall toward said plate.

9. Dynamic mixer according to claim 8, characterized in that at least one of said baffles at least partially surrounds at least one of said inlet openings.

10. Dynamic mixer according to claim 1, characterized in that the total area of said at least one outflow opening in relation to a cross-sectional area of the mixing channel at said at least one chamber is 10 to 50%.

11. Dynamic mixer according to claim 10, characterized in that the area of said at least one outflow opening in relation to the cross-sectional area of the mixing channel at said at least one chamber is no greater than 25%.

12. Use of a dynamic mixer according to claim 1 for mixing dental materials.

13. Use of a dynamic mixer according to claim 12 for mixing impression materials.

14. A dynamic mixer for the components of dental compounds, said mixer extending from a first end connectable to a device for dispensing the components to a second end defining an outlet opening for a dental compound formed from a mixture of said components, said dynamic mixer comprising:

an axially extending mixing tube which defines a radial outer limit for a mixing channel;

an end wall adjacent said first end, said end wall defining inlet openings for said components;

an axially extending rotor which defines a radial inner limit for said mixing channel, said rotor arranged for rotation about an axis within said mixer tube, said rotor comprising:

a plate axially spaced from said end wall and radially extending from said rotor to said mixing tube; and a plurality of radially projecting walls, said walls being generally perpendicular to said plate and extending from said plate toward said end wall, wherein a plurality of chambers are arranged around said axis of rotation, said chambers being axially delimited by said end wall and said plate, radially delimited by said mixing tube and said rotor, and separated by said radially projecting walls.

15. The dynamic mixer of claim 14, wherein said plate defines an outflow opening for each said chamber.

16. The dynamic mixer of claim 15, herein the total area of said outflow openings is between 10 and 50% of a cross-sectional area of said plurality of chambers.

17. The dynamic mixer of claim 15, wherein the total area of said outflow openings no greater than 25% of a cross-sectional area of said plurality of chambers.

18. The dynamic mixer of claim 15, wherein said outflow openings are formed as radially oriented slots.

19. The dynamic mixer of claim 15, wherein said outflow openings are formed as circular openings.

20. The dynamic mixer of claim 14, herein said rotor comprises axially spaced groups of radially projecting mixer blades.

21. The dynamic mixer of claim 20, wherein the axial spacing between said groups of mixer blades varies along said axis of rotation.

22. The dynamic mixer of claim 20, wherein at least 10% of an axial length of said rotor between said plate and said outflow opening is free of mixer blades.

23. The dynamic mixer of claim 22, wherein a plurality of mixing vanes are arranged to project radially inwardly from said mixing tube at an axial location corresponding to the at least 10% of said rotor axial length that is free of mixer blades.

24. A dynamic mixer for the components of dental compounds, said mixer extending from a first end connectable to a device for dispensing the components to a second end defining an outlet opening for a dental compound formed from a mixture of said components, said dynamic mixer comprising:

an axially extending mixing tube which defines a radial outer limit for a mixing channel, said mixing tube comprising a plurality of inwardly projecting mixing vanes;

an end wall adjacent said first end, said end wall defining inlet openings for said components;

an axially extending rotor which defines a radial inner limit for said mixing channel, said rotor arranged for rotation about an axis within said mixer tube, said rotor comprising:

radially projecting groups of mixer blades fixed for rotation with said rotor, wherein said groups of mixer blades are axially spaced from each other along said rotor and a portion of said rotor is free of mixer blades with said mixing vanes arranged at an axial location corresponding to the portion of said rotor that is free of mixer blades.

25. The dynamic mixer of claim 24, wherein the axial spacing between said groups of mixer blades varies along said axis of rotation.

* * * * *

UNITED STATES PATENT AND TRADEMARK OFFICE
CERTIFICATE OF CORRECTION

PATENT NO. : 6,540,395 B2
DATED : April 1, 2003
INVENTOR(S) : Mühlbauer

It is certified that error appears in the above-identified patent and that said Letters Patent is hereby corrected as shown below:

Column 5,
Line 5, delete "herein" and replace with -- wherein --.
Line 9, after "openings" insert -- is --.

Signed and Sealed this

Twenty-ninth Day of June, 2004

JON W. DUDAS
*Acting Director of the United States Patent and Trademark Office*